US007488807B2

(12) United States Patent
Mach et al.

(10) Patent No.: US 7,488,807 B2
(45) Date of Patent: Feb. 10, 2009

(54) ANTIBODY WITH PROTEIN A SELECTIVITY

(75) Inventors: Patrick A. Mach, Shorewood, MN (US); Mara S. Reif-Wenner, Red Wing, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/562,759

(22) Filed: Nov. 22, 2006

(65) Prior Publication Data

US 2008/0118937 A1    May 22, 2008

(51) Int. Cl.
*C07K 16/00* (2006.01)
*C12P 21/08* (2006.01)
*C12N 5/06* (2006.01)
*C12N 5/16* (2006.01)
*C12N 5/00* (2006.01)

(52) U.S. Cl. .................... 530/388.4; 435/326; 435/346; 530/388.1; 530/388.2

(58) Field of Classification Search ........................ None
See application file for complete search history.

(56) References Cited

U.S. PATENT DOCUMENTS

| | | | |
|---|---|---|---|
| 4,741,900 | A | 5/1988 | Alvarez et al. |
| 5,223,409 | A | 6/1993 | Ladner et al. |
| 5,594,116 | A | 1/1997 | Niles et al. |
| 6,177,084 | B1 | 1/2001 | Foster et al. |
| 6,340,571 | B1 | 1/2002 | Merlin et al. |
| 6,841,154 | B2 | 1/2005 | Foster et al. |
| 6,994,855 | B1 | 2/2006 | Foster et al. |
| 7,122,641 | B2 | 10/2006 | Vedantham et al. |
| 2006/0051820 | A1 | 3/2006 | Horii et al. |

FOREIGN PATENT DOCUMENTS

| | | |
|---|---|---|
| JP | 63-273495 | 11/1988 |
| WO | WO 86/02358 A1 | 4/1986 |
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |

OTHER PUBLICATIONS

Ackermann et al. Biotechnology and Bioengineering 1995, 45:97-106.*
Harris et al. Biotechnology 1993 11:1293-1297.*
American Type Culture Collection, "ATTC No. 12228," organism: *Staphylococcus epidermis*; designation: FDA strain PCI 1200 [online]; Manassas, VA [retrieved on Mar. 5, 2007] Retrieved from the Internet:; 3 pgs.
American Type Culture Collection, "ATTC No. 25923," organism: *Staphylococcus aureus* subsp. *aureus* Rosenbach; designation: Seattle 1945 [online]; Manassas, VA [retrieved on Mar. 5, 2007] Retrieved from the Internet:; 4 pgs.
Ausubel et al. (eds), *Current Protocols in Molecular Biology*, vol. 1; John Wiley & Sons, Inc., New York, NY; 1994; title page, publisher's page, and table of contents only; 12 pgs.
Chothia et al., "Canonical structures for the hypervariable regions of immunoglobulins," *J. Mol. Biol.*, Aug. 20, 1987; 196(4): 901-917.
Davis et al., *Basic Methods in Molecular Biology*; McGraw-Hill Profession: New York, NY; 1986, title page, publisher's page, and table of contents only.
Decker, *Immunology Tutorials, Antibody*. [Retrieved Nov. 13, 2006]. University of Arizona. Jan. 27, 2006. Retrieved from the Internet:; 11 pgs.
Frank et al., "High-yield expression, refolding, and purification of penicillin-binding protein 2a from methicillin-resistant *Staphylococcus aureus* strain 27R." *Protein Expression and Purification*, 1995; 6:671-675.
Goding, *Monoclonal Antibodies: Principles and Practice; Production and Application of Monoclonal Antibodies in Cell Biology, Biochemistry, and Immunology*; Academic Press: New York, NY; 1986; pp. 59-103.
Harlow et al.,*Antibodies: A Laboratory Manual*; Cold Spring Harbor Laboratory Press: Cold Spring Harbor, NY; 1988; title page, publisher's page, and table of contents only, 9 pgs.
Hodgkinson et al., "Selective elution of immunoadsorbed anti-(human prolactin) immunoglobulins with enhanced immunochemical properties," *Biochem. J.*, 1982; 205:535-541.
Holliger et al., "'Diabodies': small bivalent and bispecific antibody fragments," *Proc. Nat'l Acad. Sci. USA*, Jul. 15, 1993; 90(14):6444-6448.
Introduction to Antibodies, Introduction [online]. Millipore Corporation; Temecula, CA. [Retrieved on Mar. 5, 2007]. Retrieved from the Chemicon website using Internet:;8 pgs.
Jones et al., "Replacing the complementarity-determining regions in a human antibody with those from a mouse," *Nature*, May 29-Jun. 4, 1986; 32(6069):522-525.
Kabat et al., *Sequences of Proteins of Immunological Interest*, Fifth Edition; U.S. Department of Health and Human Services: Bethesda, MD; 1991, NIH Publication No. 91-3242; title page, publisher's page, and table of contents only.
Kimball, *Biology*, 6th revised edition; Antibody Affinity [online]. Sep. 9, 2003 [Retrieved Mar. 5, 2007]. Retrieved from the Biology Pages website Internet:; 6 pgs.
Kohler and Milstein, "Derivation of specific antibody-producing tissue culture and tumor lines by cell fusion," *Eur. J. Immunol.*, Jul. 1976; 6(7): 511-519.
Kostelny et al., "Formation of a bispecific antibody by the use of leucine zippers," *J. Immunol.*, Mar. 1, 1992; 148(5):1547-1553.
Lu et al., "Penecillin-binding protein 2a from methicillin-resistant *Staphylococcus aureus*: Kinetic characterization of its interactions with beta-lactams using electrospray mass spectrometry," *Biochemistry*, May 18, 1999; 38(20): 6537-6546.

(Continued)

*Primary Examiner*—Phillip Gambel
*Assistant Examiner*—Sharon Wen
(74) *Attorney, Agent, or Firm*—Michael G. Williams

(57) ABSTRACT

Monoclonal antibodies, and antigen binding fragments thereof, which bind to Protein A of *Staphylococcus aureus* are provided.

14 Claims, No Drawings

OTHER PUBLICATIONS

Orlandi et al., "Cloning immunoglobulin variable domains for expression by the polymerase chain reaction," *Proc. Nat'l Acad. Sci. USA*, May 1989; 86(10):3833-3837.

Sambrook et al., *Molecular Cloning: A Laboratory Manual*, Books 1-3; Cold Spring Harbor Laboratory Press: Cold Spring Harbor, NY; 1989; title page, publisher's page, and table of contents only, 30 pgs.

Singer II et al., "Optimal humanization of 1B4, an anti-CD18 murine monoclonal antibody, is achieved by correct choice of human V-region framework sequences," *J. Immunol.*, Apr. 1, 1993; 150(7):2844-2857.

Smith and Petrenko, "Phage Display," *Chem. Rev.*, Apr. 1, 1997; 97(2):391-410.

Smith and Waterman, "Comparison of Biosequences," *Advances in Applied Mathematics*, 1981; 2:482-489.

Songsivilai and Lachmann, "Bispecific antibody: a tool for diagnosis and treatment of disease," *Clin. Exp. Immunol.*, Mar. 1990; 79(3):315-321.

Takeda et al., "Construction of chimaeric processed immunoglobulin genes containing mouse variable and human constant region sequences," *Nature*, Apr. 4-10, 1985; 314(6010):452-454.

Traunecker et al., "Bispecific single chain molecules (janusins) target cytotoxic lymphocytes on HIV infected cells," *EMBO J.*, Dec. 1991; 10(12):3655-3659.

Traunecker et al., "Janusin: new molecular design for bispecific reagents," *Int. J. Cancer Suppl.*, 1992; 7:51-52.

U.S. Appl. No. 60/867,102, filed on even date herewith, and entitled "Method of Preparing a Mucosal Sample," filed Nov. 22, 2006.

U.S. Appl. No. 11/562,759, filed on even date herewith, and entitled "Antibody With Protein A Selectivity," present application filed Nov. 22, 2006.

U.S. Appl. No. 11/562,747, filed on even date herewith, and entitled "Antibody With Protein A Selectivity," filed Nov. 22, 2006.

U.S. Appl. No. 60/867,089, filed on even date herewith, and entitled "Specific Antibody Selection by Selective Elution Conditions," filed Nov. 22, 2006.

U.S. Appl. No. 60/867,020, filed on even date herewith, and entitled "Inactivated and Dried Biological Preparations," filed Nov. 22, 2006.

U.S. Appl. No. 60/867,093, filed on even date herewith, and entitled "Method of Analyzing a Sample for a Microorganism," filed Nov. 22, 2006.

U.S. Appl. No. 60/867,016, filed on even date herewith, and entitled "Method of Capturing Bacterial Whole Cells," filed Nov. 22, 2006.

U.S. Appl. No. 60/867,012, filed on even date herewith, and entitled "Systems and Methods for Sample Preparation Using Caps and Vials," filed Nov. 22, 2006.

U.S. Appl. No. 60/867,098, filed on even date herewith, and entitled "Method of Analyzing a Sample for a Microorganism," filed Nov. 22, 2006.

U.S. Appl. No. 60/867,073, filed on even date herewith, and entitled "Systems and Methods for Sample Preparation Using a Fluidic Device," filed Nov. 22, 2006.

\* cited by examiner

ANTIBODY WITH PROTEIN A SELECTIVITY

BACKGROUND

*Staphylococcus aureus* is a Gram-positive bacterium that causes a variety of suppurative (pus-forming) infections and toxinoses in humans. It causes superficial skin lesions (such as boils, styes and furunculosis), more serious infections (such as pneumonia, mastitis, phlebitis, meningitis, and urinary tract infections), and deep-seated infections (such as osteomyelitis and endocarditis). *S. aureus* is a major cause of hospital acquired (nosocomial) infections of surgical wounds and infections associated with indwelling medical devices. *S. aureus* causes food poisoning by releasing enterotoxins into food, and toxic shock syndrome by releasing superantigens into the blood stream.

*S. aureus* expresses a number of factors that interfere with host defense mechanisms. One such factor is Protein A. Protein A is a surface protein of *S. aureus* which binds the Fc region of immunoglobulins. In serum, the bacteria will bind IgG molecules in an orientation on their surface which disrupts opsonization and phagocytosis. Mutants of *S. aureus* lacking protein A are more efficiently phagocytosed in vitro, and mutants in infection models have diminished virulence. Protein A binds with high affinity to human IgG1, IgG2, and IgG4 as well as mouse IgG2a, IgG2b, and IgG3. Protein A binds with moderate affinity to human IgM, IgA and IgE. It does not bind with human IgG3 or IgD, nor will it bind to mouse IgM, IgA or IgE.

SUMMARY OF THE INVENTION

The present invention includes a monoclonal antibody, and antigen binding fragment thereof, wherein the monoclonal antibody inhibits the binding of monoclonal antibody 76 to Protein A from *Staphylococcus aureus*, wherein monoclonal antibody 76 is produced by hybridoma cell line 358A76.1 as deposited with the American Type Culture Collection and assigned accession number PTA-7938.

The present invention also includes a monoclonal antibody, and antigen binding fragment thereof, wherein the monoclonal antibody binds to the same epitope of Protein A from *Staphylococcus aureus* that is recognized by monoclonal antibody 76 produced by hybridoma cell line 358A76.1 as deposited with the American Type Culture Collection and assigned accession number PTA-7938.

Also included in the present invention is a monoclonal antibody, or antigen binding fragment thereof, wherein the monoclonal antibody includes the heavy chain variable region polypeptide sequence of the antibody 76 produced by hybridoma cell line 358A76.1 as deposited with the American Type Culture Collection and assigned accession number PTA-7938. In some embodiments, the monoclonal antibody, or antigen binding fragment thereof, further includes the light chain variable region polypeptide sequence of monoclonal antibody 76 produced by hybridoma cell line 358A76.1 as deposited with the American Type Culture Collection and assigned accession number PTA-7938.

The present invention also includes a monoclonal antibody, or antigen binding fragment thereof, wherein the monoclonal antibody includes the light chain variable region polypeptide sequence of the monoclonal antibody 76 produced by hybridoma cell line 358A76.1 as deposited with the American Type Culture Collection and assigned accession number PTA-7938.

The present invention also includes a monoclonal antibody, or antigen binding fragment thereof, wherein the monoclonal antibody includes a heavy chain variable region having the complementarity determining regions (CDRs) of the heavy chain of monoclonal antibody 76 produced by hybridoma cell line 358A76.1 as deposited with the American Type Culture Collection and assigned accession number PTA-7938. In some embodiments, the monoclonal antibody, and antigen binding fragment thereof, further includes a light chain variable region having the complementarity determining regions (CDRs) of the light chain of monoclonal antibody 76 produced by hybridoma cell line 358A76.1 as deposited with the American Type Culture Collection and assigned accession number PTA-7938.

The present invention also includes a monoclonal antibody, or antigen binding fragment thereof, wherein the monoclonal antibody includes a light chain variable region having the complementarity determining regions (CDRs) of the light chain of monoclonal antibody 76 produced by hybridoma cell line 358A76.1 as deposited with the American Type Culture Collection and assigned accession number PTA-7938.

In some embodiments, the antigen binding fragment thereof of the present invention is a Fab fragment, a Fab' fragment, a F(ab)$_2$ fragment, or a Fv fragment.

The present invention also includes a composition having one or more of the monoclonal antibodies, or antigen binding fragments thereof, of the present invention.

The present invention also includes a kit having one or more of the monoclonal antibodies, or antigen binding fragments thereof, of the present invention.

Also included in the present invention are transformed B cell lines that produce the monoclonal antibodies, or antigen binding fragments thereof, of the present invention.

The present invention also includes the monoclonal antibody produced by hybridoma cell line 358A76.1 as deposited with the American Type Culture Collection and assigned accession number PTA-7938, and antigen binding fragments thereof.

The present invention also includes a composition including the monoclonal antibody produced by hybridoma cell line 358A76.1 as deposited with the American Type Culture Collection and assigned accession number PTA-7938, and antigen binding fragments thereof.

The present invention also includes hybridoma cell line 358A76.1 as deposited with the Type Culture Collection and assigned accession number PTA-7938, and progeny thereof.

The present invention also includes an isolated polynucleotide including a coding sequence for the heavy chain variable region of the monoclonal antibody produced by hybridoma cell line 358A76.1 as deposited with the American Type Culture Collection and assigned accession number PTA-7938. In some embodiments, the isolated polynucleotide includes the coding sequence for the heavy chain of the antibody produced by hybridoma cell line 358A76.1 as deposited with the American Type Culture Collection and assigned accession number PTA-7938.

The present invention also includes an isolated polynucleotide including a coding sequence for the light chain variable region of the monoclonal antibody produced by hybridoma cell line 358A76.1 as deposited with the American Type Culture Collection and assigned accession number PTA-7938. In some embodiments, the isolated polynucleotide includes the coding sequence for the light chain variable region of the monoclonal antibody produced by hybridoma cell line 358A76.1 as deposited with the American Type Culture Collection and assigned accession number PTA-7938.

The present invention includes an isolated polynucleotide having the nucleic acid sequence coding for the heavy chain, the light chain, the heavy chain variable region, the light chain variable region, or one or more complementarity determining region of a monoclonal antibody of the present invention.

The present invention also includes an expression vector including an isolated polynucleotide of the present invention.

Also included in the present invention is a host cell having an expression vector of the present invention.

The present invention also includes a method of producing a substantially purified antibody, or antigen binding fragment thereof, the method including growing a transformed B cell line of the present invention under conditions in which the antibody polypeptide, or antigen binding fragment thereof, is expressed and harvesting the expressed antibody polypeptide, or antigen binding fragment thereof.

The present invention also includes a method of producing a substantially purified antibody, or antigen binding fragment thereof, the method including growing a host cell of the present invention under conditions in which the antibody, or antigen binding fragment thereof, is expressed and harvesting the expressed antibody, or antigen binding fragment thereof.

The present invention also includes a method of screening for an antibody that binds to Protein A from *Staphylococcus aureus*, the method including selecting an antibody that binds to Protein A from *S. aureus* and further selecting for an antibody that binds to intact *S. aureus*. In some embodiments, selecting for an antibody that binds to isolated Protein A from *S. aureus* includes selecting for an antibody that remains bound to Protein A from *S. aureus* in the presence of a buffer including about 0.1 M acetic acid and about 0.5 M NaCl at about pH 4. In some embodiments, selecting for an antibody that binds to intact *S. aureus* includes selecting for an antibody that remains bound to intact *S. aureus* in the presence of a buffer including about 0.1 M acetic acid and about 0.5 M NaCl at about pH 4. In some embodiments, selecting for an antibody that binds to isolated Protein A from *S. aureus* includes selecting for an antibody that remains bound to Protein A from *S. aureus* in the presence of a buffer including about 0.1 M acetic acid and about 0.5 M NaCl at about pH 4 and selecting for an antibody that binds to intact *S. aureus* includes selecting for an antibody that remains bound to intact *S. aureus* in the presence of a buffer including about 0.1 M acetic acid and about 0.5 M NaCl at about pH 4.

The present invention also includes a method of screening for an antibody that binds to its target antigen with a high specific activity, the method including contacting a candidate antibody with the target antigen in the presence of a buffer having about 0.1 M acetic acid and about 0.5 M NaCl at about pH 4; wherein a candidate antibody that remains bound to the target antigen in the presence of a buffer having about 0.1 M acetic acid and about 0.5 M NaCl at about pH 4 binds to the target antigen with a high specific activity. In some embodiments, the target antigen is a receptor binding molecule. In some embodiments, the target antigen is a molecule that binds to immunoglobulin at a location other that the antibody combining site of the immunoglobulin. In some embodiments, the molecule that binds to immunoglobulin at a location other that the antibody combining site of the immunoglobulin is Protein A, Protein G, or a Fc receptor.

Unless otherwise specified, "a," "an," "the," and "at least one" are used interchangeably and mean one or more than one.

DETAILED DESCRIPTION OF ILLUSTRATIVE EMBODIMENTS OF THE INVENTION

The present invention relates to monoclonal antibodies that bind to Protein A of *Staphylococcus aureus* (also referred to herein as "*S. aureus*" or "Staph A"). Such antibodies are useful, for example, in the detection of *S. aureus* in a biological sample. More particularly, the invention is directed to monoclonal antibodies, and antigen binding fragments thereof, that demonstrate immunological binding characteristics of monoclonal antibody 76 as produced by hybridoma cell line 358A76.1. Murine monoclonal antibody 76 is a murine IgG2A, kappa antibody isolated from a mouse immunized with Protein A. In accordance with the Budapest Treaty, hybridoma 358A76.1, which produces monoclonal antibody 76, was deposited on Oct. 18, 2006 in the American Type Culture Collection (ATCC) Depository, 10801 University Boulevard, Manassas, Va. 20110-2209, and was given Patent Deposit Designation PTA-7938 (also referred to herein as accession number PTA-7938). The hybridoma 358A76.1 produces an antibody referred to herein as "Mab 76." Mab 76 is also referred to herein as "Mab76," "Mab-76," "MAb-76," "monoclonal 76," "monoclonal antibody 76," "76," "M76," or "M 76," and all are used interchangeably herein to refer to immunoglobulin produced by hybridoma cell line 358A76.1 as deposited with the American Type Culture Collection (ATCC) on Oct. 18, 2006, and assigned Accession No. PTA-7938.

The term "monoclonal antibody" or "monoclonal antibody composition," as used herein, refers to a population of antibody molecules that contain only one species of an antigen-binding site capable of immunoreacting with or binding to a particular epitope of Protein A of *S. aureus*. A monoclonal antibody of the present invention thus typically displays a single binding affinity for a particular epitope of Protein A of *S. aureus*. As used herein the terms "monoclonal antibody" or "monoclonal antibodies" are used interchangeably.

The present invention includes the monoclonal antibodies produced by the hybridoma cell line 358A76.1. Also included in the present invention are monoclonal antibodies produced by progeny or derivatives of this hybridoma and monoclonal antibodies produced by equivalent or similar hybridomas.

The present invention includes monoclonal antibodies that inhibit the binding of monoclonal antibody Mab 76 to Protein A of *S. aureus*. The present invention includes monoclonal antibodies that bind to the same epitope of Protein A of *S. aureus* that is recognized by monoclonal antibody Mab 76. Methods for determining if a monoclonal antibody inhibits the binding of monoclonal antibody Mab 76 to Protein A of *S. aureus* and determining if a monoclonal antibody binds to the same epitope of Protein A of *S. aureus* that is recognized by monoclonal antibody Mab 76 are well known to those skilled in the art of immunology. For example, methods including, but not limited to, those described in Example 5 may be used. The monoclonal antibodies of the present invention may demonstrate improved binding to Protein A when compared to the various polyclonal anti-Protein A antisera that are available.

An intact antibody molecule has two heavy (H) chain variable regions (abbreviated herein as VH) and two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al., Sequences of Proteins of Immunological Interest, Fifth Edition, U.S. Department of Health and Human Services, NIH Publication No. 91-3242 (1991), and Chothia et al., *J. Mol. Biol.* 196: 901-917 (1987)). Each VH and VL is composed of three CDR's and four FRs, arranged from amino-terminus to carboxy-terminus in the following order: FR1, CDR1, FR2, CDR2, FR3, CDR3, FR4.

Monoclonal antibodies of the present invention include monoclonal antibodies having the same heavy chain as Mab 76. Monoclonal antibodies of the present invention include monoclonal antibodies having the same light chain as Mab 76. Monoclonal antibodies of the present invention include monoclonal antibodies having the same heavy chain and the same light chain as Mab 76. Such monoclonal antibodies may bind to Protein A of *S. aureus*. Such monoclonal antibodies may inhibit the binding of Mab 76 to Protein A of *S. aureus*. Such monoclonal antibodies may bind to the same epitope of Protein A of *S. aureus* that is recognized by Mab 76. The present invention also includes such monoclonal antibodies containing one, two, three, four, five, six, or more amino acid substitutions in the heavy and/or the light chains which do not substantially affect binding to Protein A from *S. aureus*.

Monoclonal antibodies of the present invention include monoclonal antibodies having the same VH domain as Mab 76. Monoclonal antibodies of the present invention include monoclonal antibodies having the same VL domain as Mab 76. Monoclonal antibodies of the present invention include monoclonal antibodies having the same VH domain and the same VL domain as Mab 76. Such monoclonal antibodies may bind to Protein A of *S. aureus*. Such monoclonal antibodies may inhibit the binding of Mab 76 to Protein A of *S. aureus*. Such monoclonal antibodies may bind to the same epitope of Protein A of *S. aureus* that is recognized by Mab 76. The present invention also includes such monoclonal antibodies containing one, two, three, four, five, six, or more amino acid substitutions in the VH domain and/or VL domain which do not substantially affect binding to Protein A from *S. aureus*.

Monoclonal antibodies of the present invention include monoclonal antibodies having at least one CDR region of the VH domain of Mab 76; at least two CDR regions of the VH domain of Mab 76; or at least three CDR regions of the VH domain of Mab 76; and/or at least one CDR region of the VL domain of Mab 76; at least two CDR regions of the VL domain of Mab 76; or at least three CDR regions of the VL domain of Mab 76. Such monoclonal antibodies may bind to Protein A of *S. aureus*. Such monoclonal antibodies may inhibit the binding of Mab 76 to Protein A of *S. aureus*. Such monoclonal antibodies may bind to the same epitope of Protein A of *S. aureus* that is recognized by Mab 76. The monoclonal antibodies of the present invention further include monoclonal antibodies containing one, two, three, four, five, six, or more amino acid substitutions in one or more CDR regions which do not substantially affect binding to Protein A from *S. aureus*.

Monoclonal antibodies of the present invention include monoclonal antibodies having an amino acid sequence at least about 70%, at least about 80%, at least about 85%, at least about 90%, at least about 95%, at least about 96%, at least about 97%, at least about 98%, or at least about 99% identical to an amino acid sequence of at least one CDR region of a VH domain of the antibody expressed by hybridoma cell line 358A76.1; at least two CDR regions of a VH domain of the antibody expressed by hybridoma cell line 358A76.1; or at least three CDR regions of a VH domain of the antibody expressed by hybridoma cell line 358A76.1. Such a monoclonal antibody may bind to Protein A of *S. aureus*. Such monoclonal antibodies may inhibit the binding of Mab 76 to Protein A of *S. aureus*. Such monoclonal antibodies may bind to the same epitope of Protein A of *S. aureus* that is recognized by Mab 76.

Monoclonal antibodies of the present invention include antibodies having an amino acid sequence at least about 70%, at least about 80%, at least about 85%, at least about 90%, at least about 95%, at least about 96%, at least about 97%, at least about 98%, or at least about 99% identical to at least one CDR region of a VL domain of the antibody expressed by hybridoma cell line 358A76.1; at least two CDR regions of a VL domain of the antibody expressed by hybridoma cell line 358A76.1; or at least three CDR regions of a VL domain of the antibody expressed by hybridoma cell line 358A76.1. Such an antibody may bind to Protein A of *S. aureus*. Such an antibody may bind to the same epitope of Protein A of *S. aureus* as binds to the same epitope of Protein A from *S. aureus* that is recognized by monoclonal antibody 76.

As used herein "sequence identity" between two polypeptides is determined by comparing the amino acid sequence of one polypeptide to the sequence of a second polypeptide. When discussed herein, whether any particular polypeptide is at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

"Binding affinity" or "affinity binding" refers to the strength of the sum total of noncovalent interactions between a single binding site of a molecule (e.g., an antibody) and its binding partner (e.g., an antigen or antigenic epitope). The affinity of a molecule X for its partner Y is represented by the dissociation constant (Kd), which can generally be determined by using methods known in the art, for example, using the BIAcore biosensor, commercially available from BIAcore Inc., Piscataway, N.J. Antibodies of the present invention can be described in terms of their binding affinity for Protein A of *S. aureus*. Antibodies of the present invention include antibodies with binding affinities with a dissociation constant or $K_D$ less than or equal to $5 \times 10^{-6}$ M, less than or equal to $10^{-6}$ M, less than or equal to $5 \times 10^{-7}$ M, less than or equal to $10^{-7}$ M, less than or equal to $5 \times 10^{-8}$ M, less than or equal to $10^{-8}$ M, less than or equal to $5 \times 10^{-9}$ M, less than or equal to $10^{-9}$ M, less than or equal to $5 \times 10^{-10}$ M, less than or equal to $10^{-10}$ M, less than or equal to $5 \times 10^{-11}$ M, less than or equal to $10^{-11}$ M, less than or equal to $5 \times 10^{-12}$ M, less than or equal to $10^{-12}$ M, less than or equal to $5 \times 10^{-13}$ M, less than or equal to $10^{-13}$ M, less than or equal to $5 \times 10^{-14}$ M, less than or equal to $10^{-14}$ M, less than or equal to $5 \times 10^{-15}$ M, or less than or equal to $10^{-15}$ M.

Also included in the present invention include various antibody fragments, also referred to as antigen binding fragments, which include only a portion of an intact antibody, generally including an antigen binding site of the intact antibody and thus retaining the ability to bind antigen. Fragments can be obtained via chemical or enzymatic treatment of an intact or complete antibody or antibody chain. Fragments can also be obtained by recombinant means. Examples of antibody fragments include, for example, Fab, Fab', Fd, Fd', Fv, dAB, and F(ab')$_2$ fragments produced by proteolytic digestion and/or reducing disulfide bridges and fragments produced from an Fab expression library. Such antibody fragments can be generated by techniques well known in the art. Antibodies of the present invention can include the variable region(s) alone or in combination with the entirety or a portion of the hinge region, CH1 domain, CH2 domain, CH3 domain and/or Fc domain(s). The term "antigen-binding fragment" refers to a polypeptide fragment of an immunoglobulin or antibody that binds antigen or competes with intact antibody (i.e., with the intact antibody from which they were derived) for antigen binding (i.e., specific binding).

Monoclonal antibodies of the present invention include, but are not limited to, humanized antibodies, chimeric antibodies, single chain antibodies, single-chain Fvs (scFv), disulfide-linked Fvs (sdFv), Fab fragments, F(ab') fragments, F(ab')$_2$ fragments, Fv fragments, diabodies, linear antibodies fragments produced by a Fab expression library, fragments including either a VL or VH domain, intracellularly-made antibodies (i.e., intrabodies), and antigen-binding antibody fragments thereof.

Monoclonal antibodies of the present invention may be of any isotype. The monoclonal antibodies of the present invention may be, for example, murine IgM, IgG1, IgG2a, IgG2b, IgG3, IgA, IgD, or IgE. The monoclonal antibodies of the present invention may be, for example, human IgM, IgG1, IgG2, IgG3, IgG4, IgA1, IgA2, IgD, or IgE. In some embodiments, the monoclonal antibody may be murine IgG2a, IgG1, or IgG3. With the present invention, a given heavy chain may be paired with a light chain of either the kappa or the lambda form.

Monoclonal antibodies can be obtained by various techniques familiar to those skilled in the art. For example, spleen cells from an animal immunized with a desired antigen are immortalized, commonly by fusion with a myeloma cell (see, for example, Kohler and Milstein, *Eur. J. Immunol.* 6: 511-519 (1976); J. Goding In "Monoclonal Antibodies: Principles and Practice," Academic Press, pp 59-103 (1986); and Harlow et al., Antibodies: A Laboratory Manual, page 726 (Cold Spring Harbor Pub. (1988)). Monoclonal antibodies can be isolated and purified from hybridoma cultures by techniques well known in the art. Other known methods of producing transformed B cell lines that produce monoclonal antibodies may also be used. Monoclonal antibodies of the present invention may be produced by recombinant DNA techniques, for example, produced by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods can be used to generate human monoclonal antibodies.

As used herein, "isolated" refers to material removed from its original environment (e.g., the natural environment if it is naturally occurring), and thus is altered "by the hand of man" from its natural state.

A therapeutically useful antibody may be derived from a "humanized" monoclonal antibody. Humanized monoclonal antibodies are produced by transferring one or more CDRs from the heavy and light variable chains of a mouse (or other species) immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found, for example, in Jones et al., *Nature* 321:522 (1986) and Singer et al., *J. Immunol.* 150:2844 (1993). The constant region of a humanized monoclonal antibody of the present invention can be that from human immunoglobulin belonging to any isotype. It may be, for example, the constant region of human IgG. The framework regions of the constant region derived from human immunoglobulin are not particularly limited.

Monoclonal antibodies of the present invention include chimeric antibodies. A chimeric antibody is one in which different portions are derived from different animal species. For example, chimeric antibodies can be obtained by splicing the genes from a mouse antibody molecule with appropriate antigen specificity together with genes from a human antibody molecule of appropriate biological specificity. See, for example, Takeda et al., *Nature* 314:544-546 (1985).

The present invention includes bispecific or bifunctional antibodies. A bispecific or bifunctional antibody is an artificial hybrid antibody having two different heavy/light chain pairs and two different binding sites. Bispecific antibodies can be produced by a variety of methods including fusion of hybridomas or linking of F(ab') fragments. See, e.g., Songsivilai and Lachmann, *Clin. Exp. Immunol.* 79:315-321 (1990), and Kostelny et al., *J. Immunol.* 148:1547-1553 (1992). In addition, bispecific antibodies can be formed as "diabodies" (Holliger et al., *PNAS* USA 90:6444-6448 (1993)) or "Janusins" (Traunecker et al., *EMBO J.* 10:3655-3659 (1991) and Traunecker et al., *Int. J. Cancer Suppl.,* 7:51-52 (1992)).

Monoclonal antibodies of the present invention can be produced by an animal (including, but not limited to, human, mouse, rat, rabbit, hamster, goat, horse, chicken, or turkey), chemically synthesized, or recombinantly expressed. Monoclonal antibodies of the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Monoclonal antibodies of the present invention can be assayed for immunospecific binding by the methods described herein and by any suitable method known in the art. The immunoassays that can be used include but are not limited to competitive and non-competitive assay systems using techniques such as BIAcore analysis, fluorescence activated cell sorter (FACS) analysis, immunofluorescence, immunocytochemistry, Western blots, radio-immunoassays, enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see e.g., Ausubel et al., eds, Current Protocols in Molecular Biology, Vol. 1, John Wiley & Sons, Inc., NY (1994)).

Monoclonal antibodies of the present invention include derivatives of antibodies that are modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivatives can contain one or more non-classical amino acids.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention further provides an isolated polynucleotide molecule having a nucleotide sequence encoding a monoclonal antibody of the invention. The present invention is further directed to an isolated polynucleotide molecule having a nucleotide sequence that has at least 75%, at least 80%, at least 85%, at least 90%, at least 95%, at least 96%, at least 97%, at least 98%, or at least 99% sequence identity to nucleotide sequence encoding a monoclonal antibody of the invention. The invention also encompasses polynucleotides that hybridize under high stringency to a nucleotide sequence encoding an antibody of the invention, or a complement thereof. As used herein "stringent conditions" refer to the ability of a first polynucleotide molecule to hybridize, and remain bound to, a second, filter-bound polynucleotide molecule in 0.5 M $NaHPO_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., NY, at p. 2.10.3 (1989)). Also included in the present invention are polynucleotides that encode one or more of the CDR regions or the heavy and/or light chains of a monoclonal antibody of the present invention. General techniques for cloning and sequencing immunoglobulin variable domains and constant regions are well known. See, for example, Orlandi et al., *Proc. Nat'l Acad. Sci. USA* 86:3833 (1989).

The present invention also includes recombinant vectors including an isolated polynucleotide of the present invention. The vector can be, for example, in the form of a plasmid, a viral particle, or a phage. The appropriate DNA sequence can be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art, and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector can be used.

The present invention also includes host cells containing the above-described vectors. The host cell can be a higher eukaryotic cell, such as a mammalian or insect cell, or a lower eukaryotic cell, such as a yeast cell. Or, the host cell can be a prokaryotic cell, such as a bacterial cell, or a plant cell. Introduction of a vector construct into the host cell can be effected by any suitable techniques, such as, for example, calcium phosphate transfection, DEAE-Dextran mediated transfection, or electroporation. (Davis, L., et al., Basic Methods in Molecular Biology (1986)).

Monoclonal antibodies of the present invention can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y. (1989).

Also included in the present invention are phage display libraries expressing one or more hypervariable regions from a monoclonal antibody of the present invention, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries can be prepared, for example, using the Ph.D.™-7 Phage Display Peptide Library Kit (Catalog No. E8100S) or the Ph.D.™-12 Phage Display Peptide Library Kit (Catalog No. E8110S) available from New England Biolabs Inc., Ipswich, Mass. See also, Smith and Petrenko, *Chem. Rev.* 97:391-410 (1997).

The monoclonal antibodies of the present invention may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}I$, $^{123}I$, $^{125}I$, $^{131}I$), carbon ($^{14}C$), sulfur ($^{35}S$), tritium ($^{3}H$), indium ($^{111}In$, $^{112}In$, $^{113}mIn$, $^{115}mIn$), technetium ($^{99}Tc$, $^{99}mTc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$. Techniques for conjugating such therapeutic moieties to antibodies are well-known.

Also included in the present invention are compositions including one or more of the isolated monoclonal antibodies described herein. A composition may also include, for example, buffering agents to help to maintain the pH in an acceptable range or preservatives to retard microbial growth. A composition may include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zn-protein complexes); and/or non-ionic surfactants such as TWEEN, PLURONICS, or polyethylene glycol (PEG). As used herein, a composition is not a polyclonal antiserum obtained by immunizing an animal with Protein A or *S. aureus*.

The monoclonal antibodies of the present invention can be used in both in vitro and in vivo diagnostic and therapeutic methods. Also included in the present invention are such in vitro and in vivo diagnostic and therapeutic methods.

The invention also provides a kit including the monoclonal antibodies of the present invention. The kit can include one or more containers filled with one or more of the monoclonal antibodies of the invention. Additionally, the kit may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide.

The present invention includes a method of screening for an antibody the binds to Protein A from *S. aureus* by selecting for both an antibody that binds to Protein A from *S. aureus* and selecting for an antibody that binds to intact *S. aureus*. These selections may take place in any order. For example, one may select for an antibody that binds to Protein A from *S. aureus* followed by selecting for an antibody that binds to intact *S. aureus*. Or, one may select for an antibody that binds to intact *S. aureus* followed by selecting for an antibody that binds to Protein A from *S. aureus*. Additional selection or screening steps may be included. Selecting for an antibody that binds to isolated Protein A from *S. aureus* and selecting for an antibody that binds to intact *S. aureus* may be performed under any of the wide variety of conditions available to one of skill in the art of immunology. For example, selecting for an antibody that remains bound to Protein A from *S. aureus* and/or selecting for an antibody that binds to intact *S. aureus* may take place in the presence of a buffer having about 0.1 M acetic acid and about 0.5 M NaCl at about pH 4. Other buffers having a pH and ionic strength similar to a buffer having about 0.1 M acetic acid and about 0.5 M NaCl at about pH 4 may be used.

The present invention includes methods of screening for an antibody that binds to its target antigen with a high specific activity, the method including contacting a candidate antibody with the target antigen in the presence of a buffer having about 0.1 M acetic acid and about 0.5 M NaCl at about pH 4, wherein a candidate antibody that remains bound to the target antigen in the presence of a buffer having about 0.1 M acetic acid and about 0.5 M NaCl at about pH 4 binds to the target antigen with a high specific activity. Other buffers having a pH and ionic strength similar to a buffer having about 0.1 M acetic acid and about 0.5 M NaCl at about pH 4 may be used. Additional selection or screening steps may be included. In some cases, the target antigen may be a receptor binding molecule. In some cases, the target antigen may be a molecule that binds to immunoglobulin at a location other that the antibody combining site of the immunoglobulin. Examples of such molecules that bind to immunoglobulin at a location other that the antibody combining site of the immunoglobulin include, but are not limited to, Protein A, Protein G, and other bacterial proteins that bind to the Fc portion of immunoglobulins, and Fc receptors. Fc receptors are receptors on hemopoietic cells, such as macrophages, neutrophils and mast cells, which bind to the Fc region of an immunoglobulin. Examples of Fc receptors include FcγRI (CD64), FcγRII-A (CD32), Fcγ RII-B2 (CD32), Fcγ RII-B1 (CD32), Fcε RIII (CD16), and Fcα RI Fcα RI.

The present invention is illustrated by the following examples. It is to be understood that the particular examples, materials, amounts, and procedures are to be interpreted broadly in accordance with the scope and spirit of the invention as set forth herein.

EXAMPLES

Example 1

Production of Anti-Protein A Monoclonal Antibodies

Immunization Protocol

Five female Swiss Webster mice (2.6-months old) were used in this procedure. The Protein A antigen used as an antigen for immunization was obtained from Zymed Laboratories, a subsidiary of Invitrogen, Inc. (Carlsbad, Calif.). For the screening process, the mice were bled two weeks after each immunization booster and the non-pooled samples were checked for anti-Protein A antibodies according to the protocol described below. Table 1 lists the immunization treatment protocol.

TABLE 1

Treatment protocol to generate immune cells producing anti-Protein A antibodies. The priming immunization was administered on Day 0.

| Days Post-Immunization | Treatment |
|---|---|
| 0 | Inject 0.1 mL antigen (Ag) (250 μg/mL) and 0.1 mL Complete Freund's Adjuvant intraperitoneally (I.P.) |
| 21 | Inject 0.1 mL Ag and 0.1 mL Incomplete Freund's Adjuvant (IFA) I.P. |
| 35 | Bleed all mice. Do not pool. Screen for specific antibody. |
| 42 | Inject 0.1 mL Ag and 0.1 mL IFA I.P. |
| 56 | Bleed all mice. Do not pool. Screen for specific antibody. |
| 63 | Inject 0.1 mL Ag and 0.1 mL IFA I.P. |

TABLE 1-continued

Treatment protocol to generate immune cells producing anti-Protein A antibodies. The priming immunization was administered on Day 0.

| Days Post-Immunization | Treatment |
|---|---|
| 77 | Bleed all mice. Do not pool. Screen for specific antibody. |
| 215 | Select mouse producing anti-Protein A antibodies |
| 215 | Inject 0.1 mL Ag I.P. Inject 0.1 mL Ag intravenously (IV). |
| 216 | Inject 0.1 mL Ag I.P. Inject 0.1 mL Ag IV. |
| 217 | Inject 0.2 mL Ag IV. |
| 218 | Bleed mouse for antibody screening. Sacrifice mouse for splenectomy and cell fusion. |

Fusion Protocol

The mouse selected for fusion was boosted with the same dose of antigen used in previous immunizations. The booster regime was administered over the four-day period prior to splenectomy and cell fusion, as shown in Table 1 above.

On the day of fusion the selected mouse was sacrificed and the spleen was removed aseptically. The spleen was minced using forceps and strained through a sieve. The cells were washed twice using IMDM medium (Iscove's Modified DMEM with L-glutamine and 25 mM HEPES, Cellgro catalog number 10-016-CM; Mediatech, Inc., Hemdon, Va.) and counted using a hemocytometer. The mouse myeloma cell line P3x63Ag8.653 was removed from static log-phase culture. The cell were washed with IMDM twice and counted using a hemocytometer. Myeloma and spleen cells were mixed in a 1:5 ratio and centrifuged. The supernatant was discarded. The cell pellet was gently resuspended by tapping the bottom of the tube. One milliliter of a 50% solution of PEG (MW 1500) was added (drop by drop) over a period of 30 seconds. The pellet was mixed gently for 30 seconds using a pipette. The resulting cell suspension was allowed to stand undisturbed for another 30 seconds. One milliliter (mL) of IMDM was added over a period of one minute, followed by the dropwise addition of two mL of IMDM over a period of two minutes. Another five ML of IMDM was added immediately the two-minute period. The resulting cell suspension was left undisturbed for 5 minutes.

The cell suspension was centrifuged at room temperature for 10 minutes at 1200 rpm. The pellet was resuspended in HAT medium (IMDM containing 10% FBS, 2 mM L-glutamine, 0.6% 2-mercaptoethanol (0.04% solution), hypoxanthine, aminopterin, thymidine, and 10% Origen growth factor). The cells were resuspended to $1 \times 10^6$ cells per milliliter. Cell suspensions were plated into 96-well plates. Two hundred microliters (or approximately $2 \times 10^5$ cells) were added to each well. The 96-well plates were incubated at 37° C. in a 7% $CO_2$ atmosphere with 100% humidity.

Seven days after the fusion, the media was removed and replaced with IMDM containing 10% FBS, 2 mM L-glutamine, 0.6% 2-mercaptoethanol stock (0.04%), hypoxanthine and thymidine.

Hybridoma Expansion Protocol

Fourteen days after fusion, the supernatant was taken from wells with growing hybridoma colonies. The volume of supernatant in each well was approximately 150-200 microliters. This supernatant was tested for specific antibody using the same assay (described below) that was used to screen the sera.

Positive hybridoma colonies were transferred from the 96-well plate to a 24-well plate and 1.8 mL of IMDM containing 20% FBS, 10% Origen Cloning Factor, 2 mM L-glutamine and 0.6% 2-mercaptoethanol stock (0.04%) was added to each well. The 24-well plates were incubated as described for the 96-well plates above. Five days later, the supernatant from 24-well plate was tested to confirm the presence of specific antibody.

Cells from positive wells were expanded in T-25 and T-75 flasks (Corning Flasks, Corning, N.Y.). Five vials (1 mL each) of the cells from T-75 flasks were frozen in liquid nitrogen. Cells from positive wells were cloned by limiting dilution, i.e., hybridoma cells were plated onto 96-well plates at a density of 0.25 cells per well. Growing colonies were tested 10-14 days later using the same assay that was used to initially select the hybridomas. The subclone cells were expanded to 24-well plates and, subsequently, T-25, T-75, and T-162 flasks. Vials of subclone cells were frozen as described above.

Example 2

Screening Assay for Anti-Protein A Antibody

Phase 1—Binding to Protein A

All procedures were performed at room temperature unless specified otherwise. Protein A and Goat anti-mouse antibody (gamma-chain specific, conjugated to horseradish peroxidase (HRP)) were obtained from Zymed Laboratories (Invitrogen, Inc., Carlsbad, Calif.). TMB (3,3',5,5'-tetramethylbenzidene), a chromogenic substrate for horseradish peroxidase enzyme activity, was obtained from Neogen Corporation (Lansing, Mich.).

Unless noted otherwise, all of the wash procedures for ELISA assays included three sequential wash volumes of 200 microliters (μL) per wash and all washes were done with PBST (phosphate buffered saline (150 mM NaCl in 10 mM sodium phosphate buffer, pH 7.4) containing 0.05% w/v Tween 20).

The target antigen (100 μL of 1 μg/mL Protein A suspension in carbonate buffer, pH 9.2) was coated in each well of the ELISA plates (Immulon 2; Dynex Technologies, Inc., Chantilly, Va.) for 1 hour at 37° C. After the coating step, the wells were washed twice with PBST (phosphate buffered saline (150 mM NaCl in 10 mM sodium phosphate buffer, pH 7.4) containing 0.05% w/v Tween 20).

After discarding the last wash, coating the wells with the target antigen, nonspecific protein-binding sites in the ELISA plates were blocked. Two hundred microliters of PBST containing 2% (w/v) dehydrated skim milk (blotto solution) were added to each well. The plates were incubated at 37° C. for 1 hour. The blotto solution was discarded. Antibody solution (100 μL/well, diluted in acetate buffer (0.1 M acetic acid and 0.5 M NaCl pH 4.0)) was added to each well. The plates were incubated for 1-2 hours at 37° C. After incubation, the wells were washed 3 times with PBST.

One hundred microliters of an appropriate dilution of Goat anti-mouse antibody-HRP conjugate in the blotto solution was added to each well and incubated at 37° C. for 1-2 hours. After this incubation period, the conjugate solution was removed and the wells were washed 3 times with PBST. After removing the last wash, 100 μL of TMB (Kblue, Neogen Cat No. 300199) was added to each well and the plates were held at room temperature for 1-10 minutes to observe the development of blue color. The relative HRP enzyme activity in each well was measured in a plate reader by absorbance of a 650 nm wavelength light source. Of the more than 1000 hybridoma cells lines screened, the eight cell lines that produced antibody with the highest Protein A-binding activity were selected for further screening.

Phase 2—Binding to *Staphylococcus aureus* Cells

Hybridoma cells lines that produced higher-affinity Protein A-binding antibodies were tested for their ability to bind to intact cells of *Staphylococcus aureus* and *Staphylococcus epidermidis*. The bacterial strains used in this example, *S. aureus* (ATCC 25923) and *S. epidermidis* (ATCC 12228) were obtained from the American Type Culture Collection (Manassass, Va.). Reagents and procedures for binding the antigen, washing the wells, blocking the nonspecific protein binding sites, and detecting the antigen-bound monoclonal antibody were as described in Example 5 with the exception that the antigens used in this example were washed, intact whole cells of *S. aureus* or *S. epidermidis*, rather than the Protein A antigen used in Example 5.

Bacterial cultures used for antigen preparation were grown overnight at 37° C. in Tryptic Soy Broth. The cell suspensions were washed three times by centrifuging the suspension at 10,600 k×g for 10 minutes at 4° C., decanting the supernatant, and resuspending the pellet in 100 mM sodium bicarbonate, pH 9.5. After the final wash, the cells were suspended in the sodium bicarbonate buffer to approximate cell densities of $10^7$, $10^6$, and $10^5$ colony-forming units per milliliter. These suspensions were used as antigen to coat 96-well plates. Control solutions, containing 1.0, 0.1, and 0.01 mg/mL, respectively, purified Protein A were coated into several wells of each plate.

Streptavidin-conjugated alkaline phosphatase was obtained from Jackson Immunoresearch (West Grove, Pa.) and was diluted to a working concentration of 0.5 µg/mL prior to use. The alkaline phosphatase chromogenic substrate, pNPP, was obtained from KPL (Gaithersberg, Md.). Anti-protein A monoclonal antibody SPA-27 ant its corresponding biotin-conjugated derivative were obtained from Sigma Chemical Company (St. Louis, Mo.).

Bacterial suspensions and Protein A controls were added to a 96-well plate (100 µL/well) and the plates were incubated at 37° C. for 1 hour. The wells were washed five times with PBS. Nonspecific protein-binding sites were blocked by adding 200 µL of a blotto solution (PBST with 2% w/v nonfat dehydrated milk) and the plates were held overnight at 4° C. The plates subsequently were washed with PBST.

Unlabeled monoclonal antibody solutions were diluted to 50 µg protein/mL in acetate buffer (500 µM NaCL/100 µM sodium acetate, pH 3.5). These solutions were used to prepare serial 2-fold dilutions (to 0.78 µg protein/mL) of the antibodies in acetate buffer. For use as a positive control, biotin-conjugated SPA-27 antibody was diluted 6.25 mg/mL in acetate buffer.

One hundred microliters of each dilution of the unlabeled antibodies were transferred into duplicate wells (only one unlabeled antibody per well) and the plates were incubated at 37° C. for 1 hour. The plates were subsequently washed five times. One hundred microliters of the diluted, biotin-conjugated antibody was added to the wells and the plates were incubated at 37° C. The wells were washed with PBST.

After washing the wells, 100 µL of streptavidin-alkaline phosphatase conjugate, diluted in blotto solution, was added to each well and the plates were incubated at 37° C. for 1 hour. After washing the wells, 100 µL of 5% (w/v) disodium EDTA and the plates were placed in a plate reader, where the absorbance at 405-nm wavelength was read.

The hybridoma supernatants were diluted 1:50, 1:500, and 1:5000 in sodium acetate buffer (500 µM NaCL/100 µM sodium acetate, pH 3.5) for the binding assay. After the binding reaction, the amount of antibody bound to the immobilized bacteria was measured using the alkaline phosphatase-conjugated antibody and detection reagents described in Example 5. The results showed that Mab 76 had a binding affinity for *S. aureus* cells that was approximately 3-fold higher than the average binding affinity of the other clones in this screening assay.

Example 3

Determination of Monoclonal Antibody Isotype

A commercial kit was used to identify the antibody isotype and subclass. The ISOSTRIP Mouse Monoclonal Antibody Isotyping Kit (Roche Diagnostics, Indianapolis, Ind.) was used according to the manufacturer's instructions. The results indicated that Mab 76 was classified as an $IgG_{2a}$ antibody. The results further indicated that the light chain isotype for the monoclonal antibodies was the kappa isotype.

Example 4

Western Blot Analysis

In this example, substantially pure Protein A was subjected to SDS/polyacrylamide gel electrophoresis and a western blotting was subsequently probed with monoclonal antibody 76 to demonstrate that the monoclonal antibody binds to Protein A. The Protein A was obtained from Zymed Laboratories and was loaded into the gel at an amount of 0.1 µg/lane. A mixture of known protein molecular weight markers was run in one of the gel lanes. The Novex NuPage 4-12% pre-cast SDS/polyacrylamide gel was obtained from Invitrogen, Inc., and the manufacturer's instructions were followed for the electrophoresis and western blotting procedures. The western blot was processed according to the manufacturer's instruction using the WesternBreeze Chromogenic Western Blot Immunodetection Kit (Invitrogen, Inc.), containing affinity-purified alkaline phosphatase-conjugated anti-mouse IgG antibody as the secondary probe and a chromogenic substrate to detect alkaline phosphatase activity. After transferring the protein from the gel to the membrane, individual lanes from the membrane were probed with monoclonal antibody Mab 76 and monoclonal antibody SPA-27 (Sigma Chemical Company, St. Louis, Mo.). Subsequently, the secondary probe was used to detect binding of the primary antibodies to Protein A bound to the membrane. The results indicated that both monoclonal antibodies detected a similar protein, approximately 50 kilodaltons (kD) in size.

Example 5

Epitope Blocking Analysis

This example demonstrates that the Protein A binding epitope for Mab76 is distinct from the binding epitope for Mab SPA-27. Protein A was obtained from Zymed Laboratories. Anti-Protein A monoclonal antibody SPA-27 and its corresponding biotin-conjugated derivative were obtained from Sigma Chemical Company (St. Louis, Mo.). Streptavidin-conjugated alkaline phosphatase was obtained from Jackson Immunoresearch (West Grove, Pa.) and was diluted to a working concentration of 0.5 µg/mL prior to use. The alkaline phosphatase chromogenic substrate, pNPP, was obtained from KPL (Gaithersberg, Md.).

Unless noted otherwise, all of the wash procedures for ELISA assays included three sequential wash volumes of 200 microliters per wash and all washes were done with PBST (phosphate buffered saline (150 mM NaCl in 10 mM sodium phosphate buffer, pH 7.4) containing 0.05% w/v Tween 20).

Protein A was diluted to 0.16 µg/mL in PBS, pH 7.2, added to a 96-well plate (100 µL/well), and the plates were incubated at 37° C. for 1 hour. The wells were washed five times (200 µL per wash) with PBS. Nonspecific protein-binding sites were blocked by adding 200 µL of a blotto solution (see Example 2) (PBS with 0.05% w/v Tween 20 and 2% w/v nonfat dehydrated milk) and holding the plates overnight at 4° C. The plates subsequently were washed as described previously.

Unlabeled monoclonal antibody solutions were diluted to 50 µg protein/mL in acetate buffer (500 µM NaCL/100 µM Sodium acetate, pH 3.5). These solutions were used to prepare serial 2-fold dilutions (to 0.78 µg protein/mL) of the antibodies in acetate buffer. Biotin-conjugated SPA-27 antibody was diluted to 6.25 mg/mL in acetate buffer.

One hundred microliters of each dilution of the unlabeled antibodies were transferred into duplicate wells (only one unlabeled antibody per well) and the plates were incubated at 37° C. for 1 hour. The plates were subsequently washed five times as described above. One hundred microliters of the diluted, biotin-conjugated antibody was added to the wells and the plates were incubated at 37° C.

After washing the wells, 100 µL of streptavidin-alkaline phosphatase conjugate, diluted in blotto solution, was added to each well and the plates were incubated at 37° C. for 1 hour. After washing the wells, 100 µL of the pNPP substrate solution was added to each well and the plates were held at room temperature for 10 minutes. The alkaline phosphatase reaction was stopped by adding 100 µL of 5% (w/v) disodium EDTA and the plates were place in a plate reader, where the absorbance at 405-nm wavelength was read.

The results showed that, at concentrations of unlabelled SPA-27 antibody greater than about 12.5 mg/mL, there was a significant decrease in the binding of labeled SPA-27 antibody. These results indicate that the binding of biotin-conjugated SPA-27 monoclonal antibody to protein A is inhibited by the binding of unlabeled SPA-27 monoclonal antibody.

In contrast, concentrations of up to 50 mg/mL Mab 76 did not significantly decrease the binding of labeled SPA-27 antibody to the wells coated with Protein A. These results indicate that the binding of biotin-conjugated SPA-27 monoclonal antibody to protein A is not inhibited by the binding of Mab 76. These results indicate that the Mab 76 monoclonal antibody recognizes a different binding epitope on the Protein A molecule than that recognized by the SPA-27 monoclonal antibody.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

For any method disclosed herein that includes discrete steps, the steps may be conducted in any feasible order. And, as appropriate, any combination of two or more steps may be conducted simultaneously.

What is claimed is:

1. A monoclonal antibody and antigen binding fragment thereof which binds to the same epitope of Protein A from *Staphylococcus aureus* that is recognized by monoclonal antibody 76, produced by hybridoma cell line 358A76.1 as deposited with the American Type Culture Collection and assigned accession number PTA-7938.

2. A monoclonal antibody, or antigen binding fragment thereof, which binds to Protein A of *S. aureus*, wherein the monoclonal antibody comprises the heavy chain variable region polypeptide sequence of monoclonal antibody 76 produced by hybridoma cell line 358A76.1 as deposited with the American Type Culture Collection and assigned accession number PTA-7938.

3. The monoclonal antibody, or antigen binding fragment thereon of claim 2, wherein the monoclonal antibody further comprises the light chain variable region polypeptide sequence of monoclonal antibody 76 produced by hybridoma cell line 358A76.1 as deposited with the American Type Culture Collection and assigned accession number PTA-7938.

4. A monoclonal antibody, or antigen binding fragment thereof, which binds to Protein A of *S. aureus*, wherein the monoclonal antibody comprises the light chain variable region polypeptide sequence of monoclonal antibody 76 produced by hybridoma cell line 358A76.1 as deposited with the American Type Culture Collection and assigned accession number PTA-7938.

5. A monoclonal antibody, or antigen binding fragment thereof, which binds to Protein A of *S. aureus*, wherein the monoclonal antibody comprises:
   a heavy chain variable region comprising the complementarity determining regions (CDRs) of the heavy chain of monoclonal antibody 76 produced by hybridoma cell line 358A76.1 as deposited with the American Type Culture Collection and assigned accession number PTA-7938.

6. The monoclonal antibody, and antigen binding fragment thereof, of claim 5, wherein the monoclonal antibody further comprises:
   a light chain variable region comprising the complementarity determining regions (CDRs) of the light chain of monoclonal antibody 76, produced hybridoma cell line 358A76.1 as deposited with the American Type Culture Collection and assigned accession number PTA-7938.

7. A monoclonal antibody, or antigen binding fragment thereof, which binds to Protein A of *S. aureus*, wherein the monoclonal antibody comprises:
   a light chain variable region comprising the complementarity determining regions (CDRs) of the light chain of monoclonal antibody 76 produced by hybridoma cell line 358A76.1 as deposited with the American Type Culture Collection and assigned accession number PTA-7938.

8. The antigen binding fragment thereof of claim 1, wherein the antigen-binding fragment thereof is selected from the group consisting of a Fab fragment, a Fab' fragment, a F(ab)$_2$ fragment, and a Fv fragment.

9. A composition comprising the monoclonal antibody, or antigen binding fragment thereof, of claim 1.

10. A kit comprising the monoclonal antibody, or antigen binding fragment thereof, of claim 1.

11. A transformed B cell line that produces the monoclonal antibody, or antigen binding fragment thereof, of claim 1.

12. The monoclonal antibody, which binds to Protein A of *S. aureus*, produced by hybridoma cell line 358A76.1 as deposited with the American Type Culture Collection and assigned accession number PTA-7938, and antigen binding fragments thereof.

13. A composition comprising the monoclonal antibody of claim 12.

14. A hybridoma cell line as deposited with the American Type Culture Collection and assigned accession number PTA-7938, and progeny thereof, which express the monoclonal antibody of claim 1.

* * * * *